United States Patent [19]

Weinstock et al.

[11] Patent Number: 5,395,847
[45] Date of Patent: Mar. 7, 1995

[54] IMIDAZOLYL-ALKENOIC ACIDS

[75] Inventors: Joseph Weinstock, Phoenixville; Dimitri E. Gaitanopoulos, Eaglesville, both of Pa.

[73] Assignee: SmithKline Beecham Corporation, Philadelphia, Pa.

[21] Appl. No.: 269,454

[22] Filed: Jun. 30, 1994

Related U.S. Application Data

[63] Continuation-in-part of Ser. No. 161,380, Dec. 2, 1993, abandoned.

[51] Int. Cl.$^6$ .................. C07D 409/12; A61K 31/415
[52] U.S. Cl. ................................... 514/397; 548/315.1
[58] Field of Search ....................... 548/315.1; 514/397

[56] References Cited

U.S. PATENT DOCUMENTS 5,185,351 2/1993 Finkelstein ................... 514/341

FOREIGN PATENT DOCUMENTS 9220651 11/1992 WIPO .

Primary Examiner—Robert Gerstl
Attorney, Agent, or Firm—Mary E. McCarthy; Stephen Venetianer; Edward T. Lentz

[57] ABSTRACT

Angiotensin II receptor antagonists having tile formula:

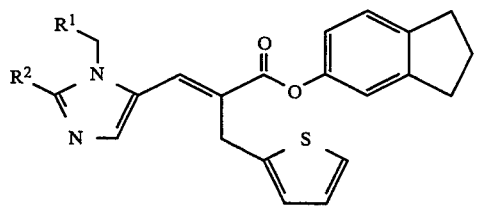

or a pharmaceutically acceptable salt thereof which are useful in regulating hypertension and in the treatment of congestive heart failure, renal failure, and glaucoma, pharmaceutical compositions including these antagonists, and methods of using these compounds to produce angiotensin II receptor antagonism in mammals. These antagonists function as prodrugs in vivo.

11 Claims, No Drawings

IMIDAZOLYL-ALKENOIC ACIDS

This is a continuation-in-part of application Ser. No. 08/161,380, filed on Dec. 2, 1993 now abandoned.

present invention relates to new imidazolyl-alkenoic acids which are angiotensin II receptor antagonists and are useful in regulating hypertension induced or exacerbated by angiotensin II, and in the treatment of congestive heart failure, renal failure, and glaucoma. This invention also relates to pharmaceutical compositions containing these compounds and methods for using these compounds as antagonists of angiotensin II, as antihypertensive agents and as agents for treating congestive heart failure, renal failure, and glaucoma. The compounds of this invention also function as prodrugs in vivo.

BACKGROUND OF THE INVENTION

The class of peptide pressor hormone known as angiotensin is responsible for a vasopressor action that is implicated in the etiology of hypertension in man. Inappropriate activity of the renin-angiotensin systems appears to be a key element in essential hypertension, congestive heart failure and in some forms of renal disease. In addition to a direct action on arteries and arterioles, angiotensin II (AID, being one of the most potent endogenous vasoconstrictors known, exerts stimulation on the release of aldosterone from the adrenal cortex. Therefore, the renin-angiotensin system, by virtue of its participation in the control of renal sodium handling, plays an important role in cardiovascular hemeostasis.

Interruption of the renin-angiotensin system with converting enzyme inhibitors, such as captopril, has proved to be clinically useful in the treatment of hypertension and congestive heart failure (Abrams, W. B., et al., (1984), *Federation Proc.*, 43, 1314). The most direct approach towards inhibition of the renin-angiotensin system would block the action of AII at the receptor. Compelling evidence suggests that AII also contributes to renal vasoconstriction and sodium retention that is characteristic of a number of disorders such as heart failure, cirrhosis and complications of pregnancy (Hollenberg, N. K., (1984), *J. Cardiovas, Pharmacol.*, 6, S176). In addition, recent animal studies suggest that inhibition of the renin-angiotensin system may be beneficial in halting or slowing the progression of chronic renal failure (Anderson, S., et al., (1985), *J. Clin. Invest.*, 76, 612). Also, a recent patent application (South African Patent Application No. 87/01,653) claims that AII antagonists are useful as agents for reducing and controlling elevated intraocular pressure, especially glaucoma, in mammals.

The compounds of this invention inhibit, block and antagonize the action of the hormone AII, and are therefore useful in regulating and moderating angiotensin induced hypertension, congestive heart failure, renal failure and other disorders attributed to the actions of AII. When compounds of this invention are administered to mammals, the elevated blood pressure due to AII is reduced and other manifestations based on AII intercession are minimized and controlled. The compounds of this invention are also expected to exhibit diuretic activity. The compounds of this invention also act as prodrugs in vivo.

Recognition of the importance of blocking and inhibiting the actions of AII has stimulated other efforts to synthesize antagonists of AII. The following references have disclosed imidazole derivatives which are described as having AII blocking activity and useful as hypotensive agents.

Furukawa et al., U.S. Pat. No. 4,340,598 discloses imidazol-5-yl-acetic acids and imidazol-5-yl-propanoic acids. Specifically, the discloser includes 1-benzyl-2-n-butyl-5-chloroimidazole-4-acetic acid and 1-benzyl-2-phenyl-5-chloroimidazole-4-propanoic acid.

Furukawa, et al., U.S. Pat. No. 4,355,040 discloses substituted imidazole-5-acetic acid derivatives. A compound specifically disclosed is 1-(2-chlorobenzyl)-2-n-butyl-4-chloroimidazole-5-acetic acid.

Carini et al. in EP 253,310 disclose certain imidazolyl-propenoic acids. Two intermediates described in this patent are ethyl 3-[1-(4-nitrobenzyl)-2-butyl-4-cholorimidazol-5-yl]propenoate and ethyl 3-[2-butyl-4-chloro-1-(4-aminobenzyl)imidazol-5-yl]propenoate.

Also, Wareing, in PCT/EP 86/00297, discloses as intermediates certain imidazolylpropenoate compounds. On page 62, Formula (CX) is ethyl 3-[1(-4-fluorophenyl)-4-isopropyl-2-phenyl- 1H-imidazol-5-yl]-2-propenoate.

DESCRIPTION OF THE INVENTION

The compound of the present invention is a blocker of angiotensin II receptors, functions as a prodrug in vivo and is represented by the following Formula (I):

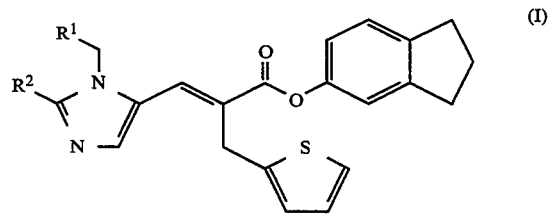

wherein:

R$^1$ is 4-carboxy-1-naphthalenyl or 4-carboxyphenyl; and

R$^2$ is C$_{2-8}$alkyl, C$_{2-8}$alkoxy, or C$_{2-8}$alkylthio;

or a pharmaceutically acceptable salt thereof.

Preferred compounds of this invention are represented by Formula (I) when:

R$^1$ is 4-carboxy-1-naphthalenyl or 4-carboxyphenyl; and

R$^2$ is C$_{2-8}$alkyl;

or a pharmaceutically acceptable salt thereof.

The E isomers (trans stereochemistry of the carboxylindanyl and imidazole group) are generally more active and, thus, are preferred over the Z isomers (cis).

A preferred compound of this invention is (E)-α-[[2-n-butyl-1-[(4-carboxyphenyl)methyl]-1H-imidazole-5-yl]methylene]-2-thiophenepropanoic acid indan-5-yl ester or a pharmaceutically acceptable salt thereof.

The preferred compound of this invention is (E)-α-[[2-n-butyl-1-[(4-carboxy-1-naphthalenyl)methyl]-1H-imidazol-5-yl]methylene]-2-thiophenepropanoic acid indan-5-yl ester or a pharmaceutically acceptable salt thereof.

The most preferred compound of this invention is (E)-α[[-2-n-butyl-1-[(4-carboxy-1-naphthalenyl)methyl]-1H-imidazol-5-yl]methylene]-2-thiophenepropanoic acid indan-5-yl ester hydrobromide.

As used herein, C$_{2-8}$alkyl means a carbon chain which is branched or unbranched with the length of the chain being 2 to 8 carbon atoms.

The invention also relates to pharmaceutical compositions comprising a pharmaceutical carrier and an effective amount of a compound of Formula (I).

Also included in the present invention are methods for antagonizing angiotensin II receptors which comprises administering to a subject in need thereof an effective amount of a compound of Formula (I). Methods of methods of treating hypertension, congestive heart failure, glaucoma, and renal failure by administering these compounds are also included in this invention.

The compounds of this invention are prepared by procedures described herein and illustrated by the examples. For example, the starting imidazole aldehydes 2-n-butyl-1-4-methyoxycarbonyl-1-naphthaleneyl)-methyl-1H-imidazole-5-aldehyde and 2-n-butyl-1-(4-methoxycarbonylphenyl)methyl-1H-imidazole-5-aldehyde are known in the art and are prepared by known procedures (Finkelstein, et al., U.S. Pat. No. 5,185,351, issued Feb. 9, 1993). The methyl ester derivative of the 4-carboxy group of R$^1$, wherein R$^1$ is as defined in Formula (I), is hydrolyzed, for example, using base, such as sodium or potassium hydroxide, in a suitable solvent system, such ethanol/water or methanol/water. The carboxy group is re-protected as the benzyl ester using, for example, benzyl bromide in the presence of a base, such as potassium carbonate, in a suitable solvent, such as dimethylformamide. The aldehyde group of the benyl ester intermediate is then reacted with 2-thiopheneylmethylmalonic acid, in the presence of a base, such as piperidine, in a suitable solvent, such as benzene, to give the 5-CH=C((2-thienyl)methyl)COOH-imidazoles. The carboxy group of these 5-substituted compounds are convened to the corresponding indanyl ester derivatives in a reaction with hydroxyindanol, in the presence of an esterification catalyst, such as 4-pyrolidinepyridine, and in the presence of a coupling reagent, such as dicyclohexylcarbodiimide. The benzyl ester of the 4-carboxy group of R$^1$ is deprotected, for example, using hydrobromic acid in acetic acid, to give the corresponding carboxy compounds, which are also Formula (I) compounds.

Pharmaceutically acceptable acid addition salts of compounds of Formula (I) are formed with appropriate organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Pharmaceutically acceptable base addition salts of compounds of Formula (I) are prepared by known methods from organic and inorganic bases, including nontoxic alkali metal and alkaline earth bases, for example, calcium, lithium, sodium, and potassium hydroxide; ammonium hydroxide, and nontoxic organic bases, such as triethylamine, butylamine, piperazine, meglumine, choline, diethanolamine, and tromethamine.

Angiotensin II antagonist activity of the compounds of Formula (I) is assessed by in vitro and in vivo methods. In vitro antagonist activity is determined by the ability of the compounds to compete with $^{125}$I-angiotensin II for binding to vascular angiotensin II receptors and by their ability to antagonize the contractile response to angiotensin II in the isolated rabbit aorta. In vivo activity is evaluated by the efficacy of the compounds to inhibit the pressor response to exogenous angiotensin II in conscious rats and to lower blood pressure in a rat model of renin dependent hypertension.
Binding The radioligand binding assay is a modification of a method previously described in detail (Gunther et al., Circ. Res. 47:278, 1980). A stable clone of human AT-1 receptors expressed in the mouse cell line L h AT-1-D$_6$ is used. Cells are incubated in Tris buffer with 80 pM of 125I-angiotensin II with or without angiotensin II antagonists for 1 hour at 25° C. The incubation is terminated by rapid filtration and receptor bound $^{125}$I-angiotensin II trapped on the filter is quantitated with a gamma counter. The potency of angiotensin II antagonists is expressed as the IC$_{50}$ which is the concentration of antagonist needed to displace 50% of the total specifically bound angiotensin II. The IC$_{50}$ of the compound of Example 1 is 342 nM.
Aorta The ability of the compounds to antagonize angiotensin II induced vasoconstriction is examined in the rabbit aorta. Ring segments are cut from the rabbit thoracic aorta and suspended in organ baths containing physiological salt solution. The ring segments are mounted over metal supports and attached to force displacement transducers which are connected to a recorder. Cumulative concentration response curves to angiotensin II are performed in the absence of antagonist or following a 30-minute incubation with antagonist. Antagonist disassociation constants (K$_B$) are calculated by the dose ratio method using the mean effective concentrations.
Inhibition of pressor response to angiotensin II in conscious rats Rats are prepared with indwelling femoral arterial and venous catheters and a stomach tube (Gellai et al., Kidney Int. 15:419, 1979). Two to three days following surgery the rats are placed in a restrainer and blood pressure is continuously monitored from the arterial catheter with a pressure transducer and recorded on a polygraph. The change in mean arterial pressure in response to intravenous injections of 250 mg/kg angiotensin II is compared at various time points prior to and following the administration of the compounds intravenously or orally at doses of 0.1 to 300 mg/k g. The dose of compound needed to produce 50% inhibition of the control response to angiotensin II (IC$_{50}$) is used to estimate the potency of the compounds. The IC$_{50}$ of the compound of Example 1 is 0.053 mg/kg orally.
Antihypertensive activity The antihypertensive activity of the compounds is measured by their ability to reduce mean arterial pressure in conscious rats made renin-dependent hypertensive by ligation of the left renal artery (Cangiano et al., J. Pharmacol. Exp. Ther. 208:310, 1979). Renal artery ligated rats are prepared with indwelling catheters as described above. Seven to eight days following renal artery ligation, the time at which plasma renin levels are highest, the conscious rats are placed in restrainers and mean arterial pressure is continuously recorded prior to and following the administration of the compounds intravenously or orally. The dose of compound needed to reduce mean arterial pressure by 30 mm Hg (IC$_{30}$) is used as an estimate of potency.

The intraocular pressure lowering effects employed in this invention may be measured by the procedure described by Watkins, et al., J. Ocular Pharmacol., 1 (2):161–168 (1985).

The compounds of Formula (I) are incorporated into convenient dosage forms, such as injectable preparations, or for orally active compounds, capsules or tablets. Solid or liquid pharmaceutical carriers are employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, such as an ampoule, or an aqueous or nonaqueous liquid suspension.

For topical ophthalmolgic administration, the pharmaceutical compositions adapted include solutions, suspensions, ointments, and solid inserts. Typical pharmaceutically acceptable carriers are, for example, water, mixtures of water and water-miscible solvents such as lower alkanols or vegetable oils, and water soluble ophthalmologically acceptable non-toxic polymers, for example, cellulose derivatives such as methyl cellulose. The pharmnaceutical preparation may also contain non-toxic auxiliary substances such as emulsifying, preserving, wetting, and bodying agents, as for example, polyethylene glycols; antibacterial components, such as quarternary ammonium compounds; buffering ingredients, such as alkali metal chloride; antioxidants, such as sodium metabisulfite; and other conventional ingredients, such as sorbitan monolaurate.

Additionally, suitable ophthalmic vehicles may be used as carrier media for the present purpose including conventional phosphate buffer vehicle systems.

The pharmaceutical preparation may also be in the form of a solid insert. For example, one may use a solid water soluble polymer as the carrier for the medicament. Solid water insoluble inserts, such as those prepared from ethylene vinyl acetate copolymer, may also be utilized.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral, parenteral, or topical products.

Doses of the compounds of Formula (I) in a pharmaceutical dosage unit as described above will be an efficacious, nontoxic quantity selected from the range of 0.01–200 mg/kg of active compound, preferably 1–100 mg/kg. The selected dose is administered to a human patient in need of angiotensin II receptor antagonism from 1-6 times daily, orally, rectally, topically, by injection, or continuously by infusion. Oral dosage units for human administration preferably contain from /1 to 500 mg of active compound. Preferably, lower dosages are used for parenteral administration. Oral administration, at higher dosages, however, also can be used when safe and convenient for the patient. Topical formulations contain the active compound in an amount selected from 0.0001 to 0.1 (w/v %), preferably from 0.0001 to 0.01. As a topical dosage unit form, an amount of active compound from between 50 ng to 0.05 mg, preferably 50 ng to 5 mg, is applied to the human eye.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of Formula (I) are diuretics, particularly a thiazide diuretic, such as hydrochlorothiazide, era loop diuretic, such as furosemide, a calcium channel blocker, particularly dihydropyridine antagonists, such as nifedipine, $\beta$-adrenoceptor block, such as propranolol, renin inhibitors, such as enalkinen, and angiotensin converting enzyme inhibitors, such as captopril or enalapril.

The AII receptor antagonist compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendrofiumethiazide, chlorothalidone, chlorothiazide, clonidine, cryptenamine acetates and cryptenamine tannates, deserpidine, diazoxide, guanethidene sulfate, hydralazine hydrochloride, metolazone, metoprolol tartate, methyclothiazide, methyldopa, methyldopate hydrochloride, minoxidil, pargyline hydrochloride, polythiazide, prazosin, rauwolida serpentina, rescinnaming, sylate, benzithiazide, quinethazone, ticynafan, triamterene, acetazolamide, aminophylline, cyclothiazide, ethacrynic acid, merethoxylline procaine, sodium ethacynate, delapril hydrochloride, enalaprilat, fosinopril sodium, lisinopril, pentopril, quinapril hydrochloride, ramapril, teprotide, zofenopril calcium, diflusinal, diltizem, felodipine, nicardipine, niludipine, minodipine, nisoldipine, nitrenedipine, verapimil and the like, as well as admixtures and combinations thereof. The AII receptor antagonist compounds of this invention can also be administered in combination with a monoamine oxidase inhibitor, such as parnate.

To illustrate these combinations, the angiotensin II antagonist of this invention effective clinically in the 2.5–250 milligrams per day range can be effectively combined at levels at the 0.5–250 milligrams per day range with the following compounds at the indicated per day dose range: hydrochlorothiazide (15–200 mg), chlorothiazide (125–2000 mg), ethacrynic acid (15–200 mg), amiloride (5–20 mg), furosemide (5–80 mg), propanolol (20–480 mg) timolol maleate (5–60 mg), methyldopa (65–2000 mg), felodipine (5–60 mg), nifedipine (5–60 mg), and nitrendipine (5–60 mg). In addition triple drug combinations of hydrochlorothiazide (15–200 mg) plus amiloride (5–20 mg) pills angiotensin II antagonist of this invention (3–200 mg) or hydrochlorothiazide (15–200 mg) pills timolol maleate (5–60 mg) plus an angiotensin II antagonist of this invention (0.5–250 mg) of hydrochlorothiazide (15–200 mg) and nifedipine (5–60 mg) plus an angiotensin II antagonist of this invention (0.5–250 mg) are effective combinations to control blood pressure in patients. Naturally, these dose ranges can be adjusted on a unit basis as necessary to permit divided daily dosage and, the dose will vary depending on the nature and severity of the disease, weight of patient, special diets and other factors.

No unacceptable toxicological effects are expected when compounds of the invention are administered in accordance with the present invention.

The following examples illustrate the preparation of compounds and pharmaceutical compositions of this invention. The examples are not intended to limit the scope of this invention as defined hereinabove and as claimed hereinbelow.

EXAMPLE 1

E-α-[[2-n-butyl-1-[(4-carboxy-1-naphthaleneyl)methyl]-1H-imidazol-5-yl]methylene]-2-thiophenepropanoic Acid Indan-5-yl Ester, Hydrobromide i) 2-n-Butyl-1-(4-carboxy-1-naphthaleneyl)methyl-1H-imidazol-5-aldehyde A suspension of 15 g of 2-n-butyl-1-4-methyoxycarbonyl-1-naphthaleneyl)-methyl-1H-imidazole-5-aldehyde (U.S. Pat. No. 5,185,351) in 180 ml of ethanol was stirred for 18 hours at 25° C. with a solution of 2.74 g of sodium hydroxide dissolved in 100 ml of water. The resulting solution was concentrated under vacuum and the pH was brought to 3.43 with 10% aqueous hydrochloric acid. The resulting solid was collected by filtration and washed with water to give 14.2 g (98% yield) of yellow crystals, mp 181.5°–182.5° C.

ii) 1-(4-Benzyloxycarbonyl-1-naphthaleneyl)methyl-2-n-butyl-1H-imidazol-5aldehyde A suspension of 7.55 g of the above acid and 3.49 g of potassium carbonate in 100 ml of dimethylformamide was stirred for 40 minutes, and then 4.09 g of benzyl bromide was added all at once. After an additional 3 hours of stirring, the reaction mixture was chilled in an acetone-ice bath while 350 ml of water was added. This mixture was extracted twice with 100 ml of ethyl acetate and the ethyl acetate washed 4 times with 150 ml of water, then once with brine, and dried over magnesium sulfate. Concentration in vacuo gave 9.87 g of an oil which slowly crystallized on standing. $R_f$ 0.56 (Silica gel, 95:5 chloroform-methanol).

iii) (E)-α-[[1-(4-Benzyloxycarbonyl-1-naphthaleneyl)-methyl]-2-butyl-1H-imidazol-5-yl]methylene]-2-thiophenepropanoic acid A mixture of 9.54 g of the above ester, 13.45 g of 2-thiopheneylmethylmalonic acid, 0.55 ml of piperidine, 100 mg of benzoic acid, and 350 ml of benzene was refluxed for 3 hours using a Dean-Stark trap to remove water. Then another 7.12 g of the malonic acid was added and the reaction mixture refluxed for an additional 18 hours and then cooled. Another 13.45 g of the malonic acid, 0.55 ml of piperidine, and 31.3 ml of pyridine were added and the mixture heated for 2 hours. Then another 5 g of the malonic acid and 5.5 ml of piperidine were added and the mixture refluxed an additional 2 hours. Finally another 7.07 g of the malonic acid was added and the mixture kept at 85° for 18 hours. The reaction mixture was concentrated under vacuum to give a syrup which on trituration with hexane (3×200 ml) gave an oil. This was dissolved in ether, and when acidified with ethereal hydrochloric acid gave a solid. Trituration of this with ether several times gave a powder. This was dissolved in 600 ml of ethyl acetate which on washing with 200 ml of water formed a crystalline solid at the interface, mp 182°–184° C. These were a single component by TLC: $R_f$ 0.29 (Silica gel, 95:5 chloroform methanol with a trace of formic acid). The ethyl acetate layer was washed 3 times with water (130 ml), then with brine and dried over magnesium sulfate. Evaporation gave a residue which was dissolved in 40 ml of warm acetone and then seeded with the above crystals. Chilling gave additional crystals, mp 182°–184° C.

iv) E-α-[[1-[(4-Benzyloxycarbonyl-1-naphthaleneyl)methyl]-2-butyl-1H-imidazol-5-yl]methylene]-2-thiophenepropanoic acid indan-5-yl ester A solution of 0.37 g of dicyclohexylcarbodiimide in 5-ml of dry methylene chloride was added over a 10 minute period to a stirred solution of the above acid (0.7 g), 5-hydroxyindanol (0.18 g), and 4-pyrolidinopyridine (0.02 g) in 15 ml of dry methylene chloride. The mixture was stirred at 25° for 18 hours, and then filtered. The filtrate was concentrated under vacuum, and the residue dissolved in ether and filtered. Concentration gave an oil which on flash chromatography (177 g Silica gel, 230–400 mesh, 6:4 hexane-ethyl acetate) gave the product as a syrup. $R_f$ 0.75 (Silica gel, 95:5 chloroform-methanol).

v) E-α-[[2-n-Butyl-1-[(4-carboxy-1-naphthaleneyl)methyl]-1H-imidazol-5yl]methylene]-2-thiophenepropanoic acid indan-5-yl ester, hydrobromide A solution of 0.89 g of the above di-ester in 3.0 ml of 30% hydrobromic acid in acetic acid was allowed to stand at 25° C. for 3.5 hours. Addition of 35 ml of ether precipitated a gummy solid which was triturated with fresh ether 4 times. The residue was dissolved in 2 ml of acetone and diluted slowly with ethyl acetate which gave crystals, mp 161°–164° C. Addition of ether to the mother liquor gave additional crystals, mp 161°–164° C. Recrystallization from acetone-ethyl acetate gave crystals, mp 162°–164° C. $R_f$ 0.34 (Silica gel, 95:5 chloroform-n-methanol). Anal: Calc'd for $C_{36}H_{34}N_2O_4S \cdot HBr$: C, 64.38; H, 5.25; N, 4.17. Found: C, 64.33; H, 5.24; N, 4.08.

EXAMPLE 2

(E)-α-[[2-n-Butyl-1-[(4-carboxyphenyl)methyl]-1H-imidazole-5-yl]methylene]-2-thiophenepropanoic Acid Indan-5-yl Ester The title compound is prepared using the methods of Example 1, replacing 2-n-butyl-1-(4-methoxycarbonyl-1-naphthaleneyl)methyl-1H-imidazole-5-aldehyde with 2-n-butyl-1-(4-methoxycarbonylphenyl)methyl-1H-imidazole-5-aldehyde (U.S. Pat. No. 5,185,351).

EXAMPLE 3

An oral dosage form for administering orally active Formula (I) compounds is produced by screening, mixing and filling into hard gelatin capsules the ingredients in proportions, for example, as shown below.

| Ingredients | Amounts |
| --- | --- |
| E-α-[[2-n-butyl-1-[(4-carboxy-1-naphthaleneyl)methyl]-1H-imidazol-5-yl]methylene]-2-thiophenepropanoic acid indan-5-yl ester, hydrobromide | 100 mg |
| magnesium stearate | 10 mg |
| lactose | 100 mg |

EXAMPLE 4

The sucrose calcium sulfate dihydrate and orally active Formula (I) compounds are mixed and granulated with a 10% gelatin solution. The wet granules are screened, dried, mixed with the starch, talc and stearic acid, screened and compressed into a tablet.

| Ingredients | Amounts |
| --- | --- |
| E-α[[2-n-butyl-1-[(4-carboxy-1-naphthaleneyl)methyl]-1H-imidazol-5-yl]methylene]-2-thiophenepropanoic acid indan-5-yl ester, hydrobromide | 75 mg |
| calcium sulfate dihydrate | 100 mg |
| sucrose | 15 mg |
| starch | 8 mg |
| talc | 4 mg |
| stearic acid | 2 mg |

EXAMPLE 5

E-α-[[2-n-Butyl-1-[(4-carboxy-1-naphthaleneyl)methyl]-1H-imidazol-5yl]methylene]-2-thiophenepropanoic acid indan-5-yl ester, hydrobromide, 50 mg, is dispersed in 25 mL of normal saline to prepare an injectable preparation.

EXAMPLE 6

A topical opthamological solution for administering Formula (I) compounds is produced by mixing under sterile conditions the ingredients in proportions, for example, as shown below.

| Ingredients | Amounts (mg/mL) |
| --- | --- |
| E-α-[[2-n-butyl-1-[(4-carboxy-1-naphthaleneyl)methyl]-1H-imidazol-5-yl]methylene]-2-thiophenepropanoic acid indan-5-yl ester, hydrobromide | 1.0 |
| dibasic sodium phosphate | 10.4 |
| monobasic sodium phosphate | 2.4 |
| chlorobutanol | 5.0 |
| hydroxypropanol methylcellulose | 5.0 |
| sterile water | q.s. ad 1.0 mL |
| 1.0 N sodium hydroxide | q.s.ad pH 7.4 |

It is to be understood that the invention is not limited to the embodiments illustrated hereabove and the right to the illustrated embodiments and all modifications coming within the scope of the following claims is reserved.

What is claimed is:

1. A compound of the formula:

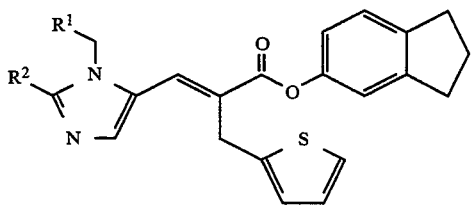

wherein:

$R^1$ is 4-carboxy-1-naphthalenyl or 4-carboxyphenyl; and $R^2$ is $C_{2-8}$alkyl, $C_{2-8}$alkoxy, or $C_{2-8}$alkylthio;

or a pharmaceutically acceptable salt thereof.

2. The compound of claim 1 which is E-α-[[2-n-butyl-1-[(4-carboxy-1-naphthalene)methyl]-1H-imidazol-5-yl]methylene]-2-thiophenepropanoic acid indan-5-yl ester or a pharmaceutically acceptable salt thereof.

3. The compound of claim 2 which is E-α-[[2-n-butyl-1-[(4-carboxy-1-naphthaleneyl)methyl]-1-H-imidazol-5-yl]methylene]-2-thiophenepropanoic acid indan-5-yl ester, hydrobromide.

4. The compound of claim 1 which is (E)-α-[[2-n-butyl-1-[(4-carboxyphenyl)methyl]-1H-imidazole-5-yl]methylene]-2-thiophenepropanoic acid indan-5-yl ester or a pharmaceutically acceptable salt thereof.

5. A pharmaceutical composition comprising a pharmaceutical carrier and a compound of claim 1.

6. A method of antagonizing angiotensin II receptors which comprises administering to a subject in need thereof an effective amount of a compound of claim 1.

7. A method of treating hypertension which comprises administering to a subject in need thereof an effective amount of a compound of claim 1.

8. A method of treating congestive heart failure which comprises administering to a subject in need thereof an effective amount of a compound of claim 1.

9. A method of treating renal failure which comprises administering to a subject in need thereof an effective amount of a compound of claim 1.

10. A method of treating glaucoma which comprises administering to a subject in need thereof an effective amount of a compound of claim 1.

11. A method of treating hypertension which comprises administering stepwise or in a physical combination with a diuretic a compound of claim 1.

* * * * *